United States Patent [19]

Kruishoop

[11] 3,975,947

[45] Aug. 24, 1976

[54] METHOD OF AND APPARATUS FOR QUANTITATIVE ANALYSIS

[75] Inventor: Johan Christiaan Willem Kruishoop, Eindhoven, Netherlands

[73] Assignee: U.S. Philips Corporation, New York, N.Y.

[22] Filed: Apr. 23, 1975

[21] Appl. No.: 570,728

[30] Foreign Application Priority Data

Apr. 24, 1974 Netherlands.................... 7405493

[52] U.S. Cl............................. 73/61.1 R; 73/1 G; 73/28

[51] Int. Cl.²......................................... G01N 27/50

[58] Field of Search................. 73/61.1 R, 61 R, 28, 73/23, 1 G

[56] References Cited
UNITED STATES PATENTS

| | | |
|---|---|---|
| 3,206,449 | 9/1965 | Van Luik, Jr....................... 73/28 X |
| 3,242,715 | 3/1966 | Hubner................................. 73/1 G |
| 3,300,282 | 1/1967 | Risk et al............................. 73/23 X |
| 3,611,790 | 10/1971 | Brouwer et al.................. 73/61.1 R |
| 3,674,435 | 7/1972 | Van Luik, Jr. et al......... 73/1 G UX |
| 3,776,023 | 12/1973 | Budd et al............................ 73/1 G |
| 3,888,112 | 6/1975 | De Leeuw et al................ 73/61.1 R |

*Primary Examiner*—Richard C. Queisser
*Assistant Examiner*—Joseph W. Roskos
*Attorney, Agent, or Firm*—Frank R. Trifari; David R. Treacy

[57] ABSTRACT

Method of measuring constituents in a fluid which may be gaseous or liquid, which dispenses with calibration procedures which are performed at the expense of the measuring time. The measuring apparatus is continuously supplied with a known amount of constituents from a calibration source, which calibration amount is mixed with the fluid to be measured. Subsequently, a part of the constituents of the mixture is led to a detector, and the resulting measuring signal is compared to a reference signal for adjusting a control device to ensure that the amount of constituents which reaches the detector is the correct value. The setting of the control device is an output signal useful in unattended measuring stations for water and air pollution.

16 Claims, 12 Drawing Figures 3,975,947

METHOD OF AND APPARATUS FOR QUANTITATIVE ANALYSIS

BACKGROUND OF THE INVENTION

1. Field of the Invention

The invention relates to a method of continuously and quantitatively determining one or more constituents of a fluid which is passed through a detector, a measuring signal being obtained at output terminals of the detector, which signal is a measure of the amount of constituents supplied to the detector.

The invention also relates to an apparatus for carrying out said method, which apparatus comprises a detector having an inlet connected in a supply line and an outlet connected in a discharge line, in which a first fluid flow control is included, which sustains a flow of fluid from a supply compartment through the detector, fluid constituents to be measured producing a measuring signal at output terminals of the detector, and further comprises a calibration source which supplies a known amount of constituents.

2. Description of the Prior Art

Methods and apparatus for quantitative analysis are known. In U.S. Pat. No. 3,611,790 it is for example described how a fluid, which may be liquid or gaseous, can be examined for the presence of certain constituents, a detector or measuring cell detecting the presence of said constituents and being capable of measuring in which concentration these substances or constituents occur. For this purpose, a stream of the fluid is passed through the detector and at specific instants the apparatus is tested for zero drift and variation of properties. This enables an accurate measurement to be conducted of the concentration of the constituents to be measured. Use is made of absorption filters which, for a zero point measurement, absorb the constituents and which are included in the supply line to the detector, and of calibration sources which, for the calibration of the measuring scale of the detector, supply a known amount of the constituents to be measured to the detector.

In some cases it may be disadvantageous that the actual measurement is to be interrupted for the calibration procedure. Especially when the detector responds slowly to concentration variations the calibration procedure will require much time. Furthermore, in the case of comparatively rapidly changing detector settings, the detectors will have to be calibrated more frequently.

SUMMARY OF THE INVENTION

The concept which underlies the invention is based on the insight that a faster and better system can be obtained when the amount of substances to be measured, which is supplied to the detector, is maintained constant. As a result of this, the detector setting remains at one point of its measuring characteristic. Deviations from this point are immediately corrected with a control system.

In a method according to the invention the amount of constituents to be measured in the fluid is continuously replenished with a known amount of the constituents from a calibration source, and least a part of the constituents of the obtained mixture is supplied to the detector. The measuring signal from the detector is compared with a reference signal and by means of a control device the amount of constituents supplied to the detector is adjusted so as to minimize the difference between the measuring signal and reference signal, the setting of the control device being a measure of the amount of constituents to be measured.

This method provides the advantage that at least one calibration procedure is dispensed with, because the concentration to be measured is continuously referred to a calibration concentration. Furthermore it is possible to dispense with switching valves or cocks in the supply lines to the detector, and non-linearity of the detector will not affect the measurement. However, it is necessary to measure the zero drift and sensitivity variation of the detector, because outside the detector an electric reference signal is used in the zero compensation method according to the invention.

Therefore, in a further embodiment of the inventive method, the measuring signal from the detector is employed as a reference signal, which is obtained when the fluid is first cleaned of constituents to be measured by means of a filter and subsequently the calibration amount of known value is added.

This measuring signal may be stored in a memory circuit, for which known and simple electronic circuit arrangements may be employed.

It is to be noted that in the case of the preceding method the measurement has to be interrupted for adjusting the correct value of the reference signal.

If this presents problems, a different embodiment of the method according to the invention may be employed, in which a known portion of the part of the constituents of the obtained mixture, which is supplied to the detector, is fed to a measuring circuit which includes a second detector, to which alternately said known portion and a known calibration amount of constituents is supplied, the detector producing a measuring signal which contains an a.c. component if the concentrations in the two flows of fluid are unequal, upon which an electrical controller adjusts said reference signal so that the a.c. component is minimized.

In this respect it is advantageous that the measurement is not interrupted and the main stream of fluid need not include any switching valves or cocks. The additional measuring and control circuit ensures that on an average the same amount of constituents is maintained in the fluid flow which passes through the detector. The response of the detector to said average amount can consequently be found back in the value of the adjusted reference voltage. Hence, this includes the zero-point drift and the variation of the detector sensitivity. Both have a very large time constant, so that it will be evident that the control loop of the described auxiliary circuit is slow, i.e. has a small bandwidth, but can be made very sensitive. Normal fluctuations in said amount supplied, to which the main control loop responds for the concentrations to be measured in the fluid, have no influence on the setting of the control loop of the auxiliary circuit.

According to the invention it is possible to make the calibration amount to be supplied variable, so that the sum of calibration amount and amount of constituents to be measured by the detector and the control device is kept constant, or to make the calibration amount to be supplied constant and passing only a part of the mixture obtained through the detector, while the control device ensures that this part contains a constant amount of constituents by control of an adjusting device.

A variable amount of calibration constituents can be obtained by the use of a variable calibration source as described in applicants co-pending U.S. Pat. Application, Ser. No. 474,809 filed May 30, 1974 or by injecting a known amount of calibration constituents by means of a calibration source into a flow of fluid from which constituents to be measured have been removed, and subsequently passing said flow through a self-diluting system which is controlled by a control device, so that a variable calibration amount to be adjusted can be introduced into the fluid flow to be measured.

Further elaborations of the method according to the invention are characterized in that a part of the mixture is passed directly to the detector and the other part via a fluid flow control and an absorption filter, the adjusting device being the fluid flow controller and the absorption filter absorbing the constituents, or in that the mixture is divided into two parts, of which one part is directly passed to the detector and the other part bypasses the detector, the division of the mixture into two parts being preferably determined by a fluid flow controller as an adjusting means.

In preferred embodiments of the apparatus according to the invention use if made of a self-diluting system, which either adjusts the calibration amounts to be supplied to the required value or adjusts the amount of constituents to be supplied to the detector to the required value. This self-diluting system consists of two parallel branches, of which a first branch transfers one part of the fluid flow directly and the other branch transfers the other part after this has been adjusted by a fluid flow controller and has been cleaned of constituents by means of an absorption filter. The fluid flow controller may be a pump, of which for example the speed is controlled by the control device. The flow controller may also be a valve, which is driven by a variable frequency with fixed pulse width or by a fixed frequency with variable pulse width. When a valve is employed at least the first branch should contain a restriction, which represents a flow resistance. Control valves or throttling cocks or valves with adjustable diaphragm may be used alternatively.

In other embodiments of the apparatus according to the invention a part of the fluid flow is passed through the detector and the other part is discharged. Preferably, a parallel branch is employed. The fluid flow controller, which determines the distribution and which is controlled by the control device, may be included in series with the detector or in the parallel branch. Control in these embodiments is consequently such that a variable flow of fluid passes through the detector with concentration variations which are inversely proportional to this flow, so that the amount of constituents supplied to the detector per unit of time is constant.

BRIEF DESCRIPTION OF THE DRAWINGS

The invention will now be described in more detail with reference to the drawing, in which

FIG. 1a shows in block-schematic form how the method according to the invention can be realized.

Figures 1A, 1B:
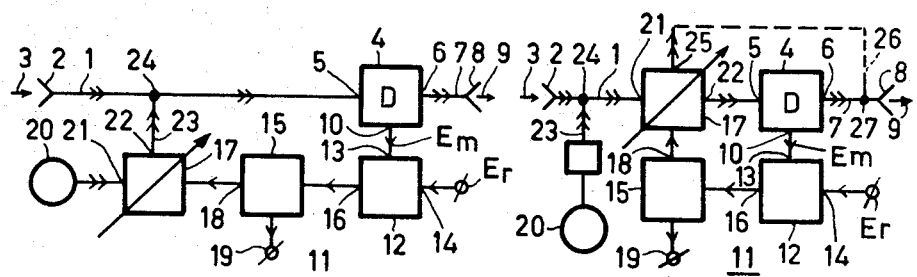
FIGS. 1a and 1b represent embodiments a and b of the invention in block-schematic form.

The supply line 1 comprises an inlet 2, where at 3 a fluid arrives from a supply compartment, which may be a vessel with liquid or the atmospheric air to be examined. The supply line 1 is connected to a detector or measuring cell 4, designated D, with an inlet connection 5 and an outlet connection 6, to which a discharge line 7 is connected which via an outlet 8 discharges the measured flow of fluid 9. In the detector D the constituents to be measured react with chemical substances, as in a coulometric measuring cell, so that at output 10 of the detector a measuring voltage designated $E_m$ is obtained, which is a measure of the amount of constituents supplied to the detector. Alternatively, the detector may be of a type which has a measuring surface which reacts with the constituents and over which the flow of fluid is passed, or it may be of an optical or chemiluminescent type or operate with magnetic waves. The fluid flow controller, which controls the flow, is not shown, but is preferably included in the discharge line 7. Furthermore, it is possible to employ the force of gravity when the fluid is a liquid. The control device 11 consists of a comparator circuit 12 with an input 13 for the measuring voltage $E_m$ and an input 14 for a reference signal designated $E_r$, which can be supplied by a suitable reference source; and an electrical controller 15, which is connected to the output 16 of comparator circuit 12, and an adjusting device 17, which is connected to the output 18 of controller 15.

The difference signal $E_M-E_r$ drives the controller 15, which produces at signal a output 18, which signal determines the setting of device 17. When the difference has become substantially zero, the drive of device 17 will not change any further. The signal from the output 18 may be employed as output signal of the measuring apparatus, for it is a measure of the fluid constituents to be measured. However, FIG. 1a shows that this control parameter is available at an output 19 of the controller 15. A calibration source 20 supplies a known amount of constituents to an inlet 21 for calibration purposes. Devices of this type are known, for example, from my co-pending application Ser. No. 474,809 referred to above; and from such U.S. Pats. as No. 2,033,427 issued Mar. 10, 1936, and No. 3,799,396 issued Mar. 26, 1974. Depending on the setting of device 17 the outlet 22 supplies a part of said known amount to the calibration line 23. Via calibration line 23 this part is supplied to the branch 24, which is located in the supply line 1. When the concentration of the fluid constituents to be measured is called Cx, to be expressed parts per million or parts per billion or micrograms per liter, and the flow $f$ of fluid in for example milliliters per minute, and the supply of calibration constituents from the calibration source m in micrograms per minute, and when the setting of device 17 is taken to be A, the following relationship is valid for the control loop of FIG. 1a:

$$f \cdot Cx + m \cdot A = \text{constant} \tag{1}$$

In FIG. 1b the calibration source 20 via calibration line 23 supplies a known amount of constituents to the main fluid stream in supply line 1. The adjusting device 17 is adjusted so by means of the controller 15 that only a part of the supplied constituents reaches the outlet 22 via inlet 21 so as to be measured in the detector D. The other part which is not measured can be discharged via an outlet 25, for example to leave the outlet 8 via a line 26 by way of a branch 27 in discharge line 7. In its simplest form the means 17 may comprise a rotary cock as adjusting element with one inlet 21 and two outlets 22 and 25, the setting of the cock determining the flow division between the outlets.

Figure 2:
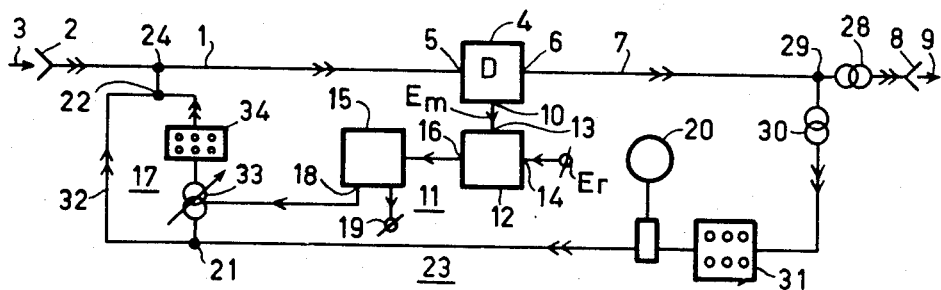
FIG. 2 shows an embodiment of an apparatus according to the invention in block-schematic form with a variable calibration flow in accordance with FIG. 1a, FIG. 3 shows a different embodiment in accordance with FIG. 1a, FIG. 4 shows an embodiment of the invention in accordance with FIG. 1b, FIGS. 5a and 5b show two different embodiments a and b in accordance with FIG. 1b.

FIG. 2 shows a further elaboration of the block diagram of FIG. 1a. The calibration line 23 and the adjusting device 17 are shown in more detail. The flow of fluid from inlet 2 to outlet 8 is controlled by a fluid flow controller 28, which is included in the discharge line 7. A part of the flow therein is branched off via a branch 29 and a flow controller 30 for the calibration line 23, which first includes an absorption filter 31, then the calibration source 20 and the adjusting device 17. The device 17 is a self-diluting system with a parallel branch 32 and a branch with fluid flow controller 33 as adjusting element, followed by an absorption filter 34. Depending on the setting of said controller 33 a part of the calibration flow in line 23 is cleaned of constituents. When the same quantities are used as in equation (1) and when the flow in calibration line 23 is taken to be $f_1$ and the part which flows through controller 33 and filter 34 $f_p$, the following applies to the control system of FIG. 2:

$$fCx + m \cdot \frac{f_1 - f_u}{f_1} = \text{constant} \qquad 2)$$

Figure 3:
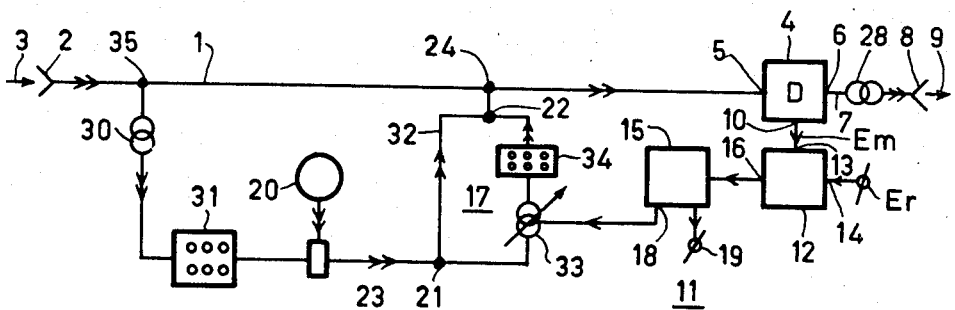

FIG. 3 shows the same system as in FIG. 2, but the inlet of the calibration line 23 is now connected to a branch 35 which is located between inlet 2 and branch 24. For this control system the following relation is valid:

$$(f - f_1) Cx + m \frac{f_1 - f_u}{f_1} = \text{constant} \qquad 3)$$

Figure 4:
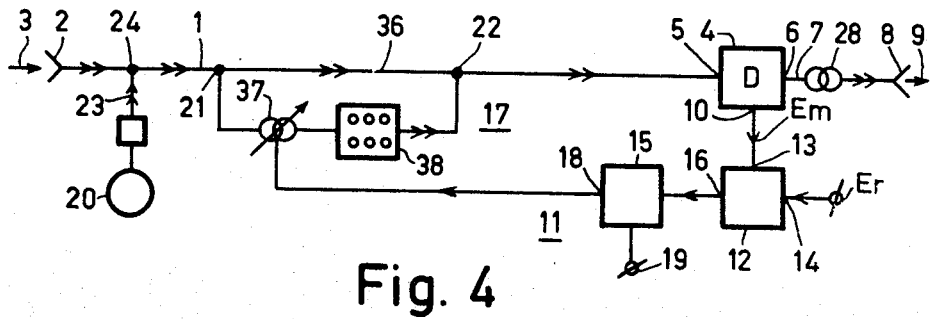

In FIG. 4 a known amount of constituents from the calibration source is introduced into the fluid flow via the branch 24 in the supply line 1. Subsequently, the amount of constituents which is supplied to the detector 4 is adjusted by the device 17 which takes the form of a self-diluting system. This system consists of a branch 36 and a branch with fluid flow controller 37 and absorption filter 38. Depending on the setting of controller 37 outlet 22 will therefore supply less constituents that are supplied to inlet 21.

When the flow through controller 37 is again $f_p$, then $$(fCx + m) \frac{f_1 - f_p}{f} = \text{constant} \qquad 4)$$

Figure 5A:
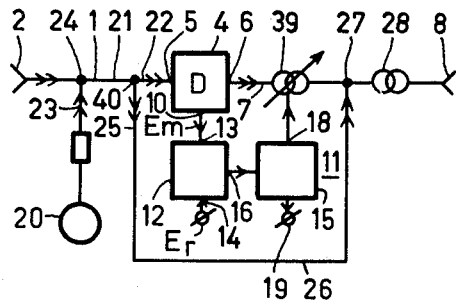

In FIG. 5a the flow of fluid is divided into two parts, of which one part is passed through the detector. For this purpose the line 1 includes a branch 40, which divides the amount of constituents in flow f at the inlet 21 into a flow $f_p$ at outlet 25, which is fed via line 26 to branch 27 in discharge line 7, and into a flow $f - f_p$ at outlet 22 for the detector 4. The flow division is determined by a flow controller 39 which is included in line 7 between outlet 6 and branch 27. Equation 4) also applies to this apparatus.

Figure 5B:
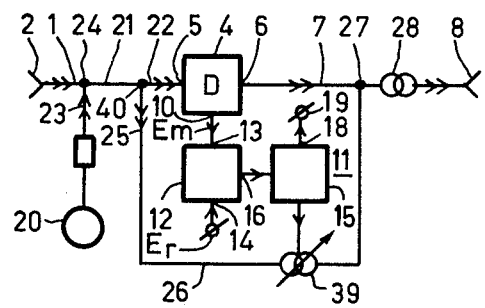

FIG. 5b is identical to FIG. 5a, but the controller 39 is now included in line 26.

Figure 6:
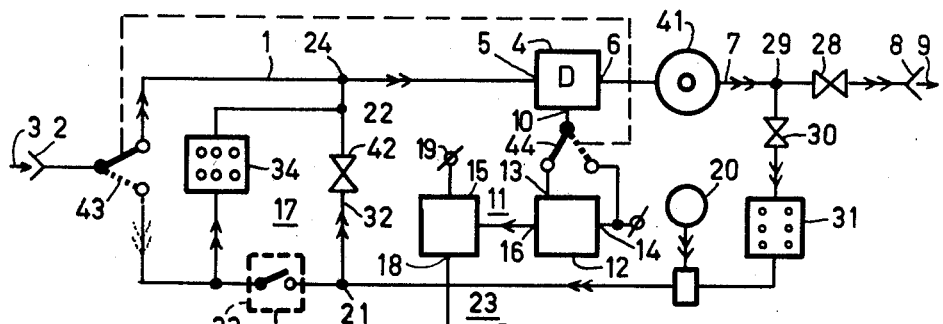
FIG. 6 shows an apparatus in accordance with FIG. 2.

FIG. 6 is a further elaboration of the apparatus of FIG. 2. In discharge line 7 a pump 41 is included and the flow controllers 28 and 30 take the form of restrictions. Pump and restrictions ensure constant flow in the lines. The dilution system 17 comprises a restriction in branch 32 and a magnetic valve 33 in the other branch as a flow controller. By driving this valve with a pulse train of variable frequency or pulse width, the variable calibration flow is obtained at outlet 22.

Equation (2) is also valid in this case if restriction 30 represents a substantially higher flow resistance than restriction 42. As the case may be, the variable restriction, which system 17 represents, may be calculated and inserted in equation (2).

FIG. 6 also shows a method of eliminating zero drift and variation of the detector sensitivity by adaptation of the reference signal $E_r$. For this supply line 1 includes a switching valve 43 after inlet 2 and a switch 44 is included between output 10 and inputs 13 and 14. In the shown position of the two switches the apparatus operates as described with reference to FIG. 2. In the dotted position the measuring signal at output 10 of detector 4 is applied to input 14 as reference signal and the fluid flow from inlet 2 is suppllied to the filter 34 so as to be cleaned of constituents. The valve 33 may be left open in this calibration condition of the apparatus, but especially when a pump is used it is desirable to avoid non-linearities by allowing a specific "zero flow" for example with a value $f_{po}$. This zero flow is also necessary in the case of low measuring concentrations and much noise in the system so as to avoid negative control signals to which the pump cannot respond. The measuring signal $E_m$, which can now be stored in a memory circuit as reference signal $E_r$ for the following measuring period of the apparatus, corresponding to:

$$n \frac{f_1 - f_{uo}}{f_1} = \text{constant of 2)} \qquad 5)$$

so that from (2) and (5) the concentration may be derived:

$$Cx = \frac{f_u - f_{uo}}{f_1 \cdot f} \qquad 6)$$

Figure 7:
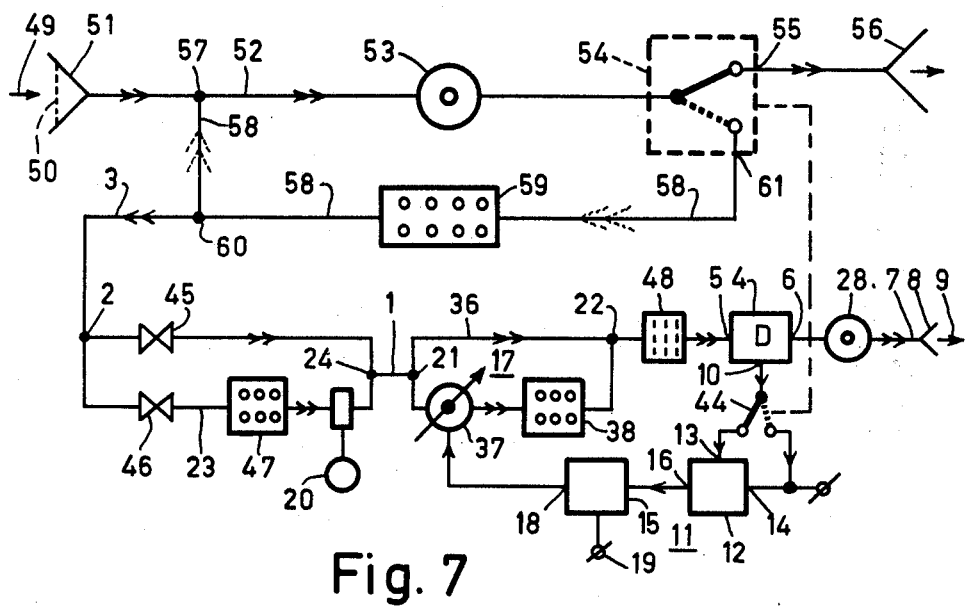
FIG. 7 shows an apparatus in accordance with FIG. 4.

FIG. 7 shows a further elaboration of FIG. 4. The supply line 1 includes a restriction 45 between the inlet 2 and the branch 24, so as to produce a pressure drop for the calibration line 23 which is also included between inlet 2 and branch 24 and which in the direction of flow includes a restriction 46, an absorption filter 47 and the calibration source 20. In the dilution system 17 the flow controller 37 is represented as a pump, which is also the case with the fluid flow controller 28 in the discharge line 7. The device 48 before the detector 4 may be a dust filter, a selective filter for passing through measuring substances and retaining substances which disturb the measurement, or a moisture dosing device, if required.

FIG. 7 also shows how the generally small amount of fluid for the measurement can be derived from a substantially larger flow of fluid. For this, a large amount of fluid is drawn in by means of a pump 53 through a line 52 via a filter 50 and an inlet nozzle 51. To the discharge outlet of the pump a switching valve 54 is connected which has an outlet 55 which is connected to an outlet 56. The line 52 has a branch 57, to which a line 58 is connected, which includes an absorption filter 59. Between branch 57 and filter 59 a branch 60 is included in line 58, to which inlet 2 of the measuring apparatus is connected. In the drawn position of the switching valve 54 and the switch 44 which is coupled thereto, the measuring stream 3 of the fluid flows from branch 57. Since in practice the apparatus of FIG. 7 will form a compact assembly, long supply lines between inlet 51 and branch 57 are permissible. This is of importance when water or air pollution is measured, because otherwise the small measuring quantity 3 would result in such small flow rates in said supply line, that constituents might settle in the supply line or reactions with the material of the supply line might become possible. Another advantage is that in the measuring system no switching valve for calibration with purified fluid is required. When valve 54 is set to outlet 61, to which the inlet of line 58 is connected, a stream of purified fluid is obtained in line 58 after the filter 59, of which again a small part 3 is used for the measuring system. The direction of flow in this case is indicated by dotted double arrows. Furthermore, it is to be noted that in spite of the substantial flow the filter 59 need not have a high filter capacity, because only the contents of the recirculation system 52, 53, 54, 58, 59 plus the consumption 3 must be purified.

Figure 8:
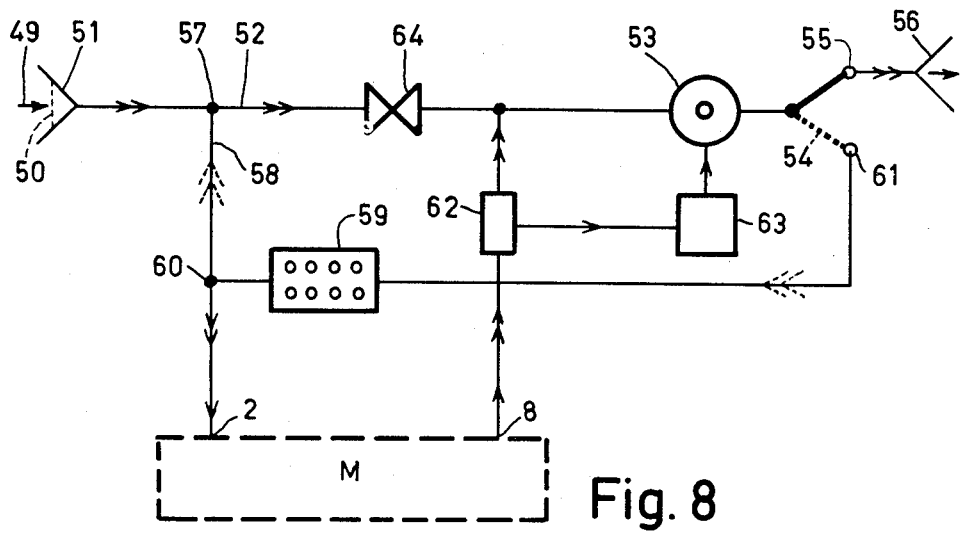
FIG. 8 shows a different embodiment of a part of FIG. 7.

FIG. 8 shows a modification of the pump system of the apparatus of FIG. 7. The fluid flow controller 28 of FIG. 7 has been replaced by a flow meter 62, which ensures that a constant flow of fluid is maintained in the measuring system M. For this purpose the output signal of flow meter 62 via a comparator and control circuit 63 controls the pump 53 so that a constant pressure drop is obtained across a restriction 64 in line 52.

Figure 9:
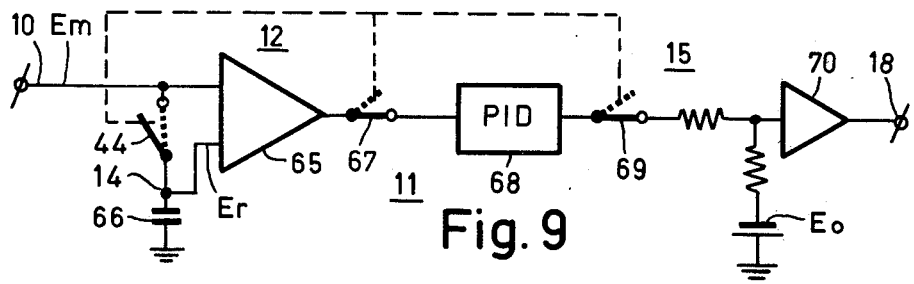
FIG. 9 shows an electrical control device.

FIG. 9 shows the electronic section of the control device 11, as this may be used in FIGS. 6, 7 and 8. The comparator circuit 12 consists of a differential amplifier 65, which with one input is connected to output 10 of the detector, for comparing the measuring voltage $E_m$ with the reference voltage $E_r$ which appears at the other input of the amplifier 65. This reference voltage is derived from a storage capacitor 66. The difference signal of the two voltages is applied via a switch 67 to an electrical controller 68, whose character is adapted to the complete control-loop, which is generally denoted by proportional-integrating-differentiating (PID). Via a switch 69 the control signal from controller 68 is applied to a summation point of an amplifier 70. Moreover, a biassing voltage $E_o$ is applied to this point. The output signal of said amplifier 70 via output 18 controls the adjusting device with the adjusting element which determines the flow $f_p$ or $f_{po}$. In the dotted position of the switches 44, 67 and 69 the PID-controller setting is maintained, the output voltage at output 18 is determined by the source $E_o$ for the flow $F_{po}$ and the reference voltage $E_r$ at capacitor 66 is adapted to the measuring voltage $E_m$, which is supplied by the detector D when a purified flow of fluid is supplied thereto.

Figure 10:
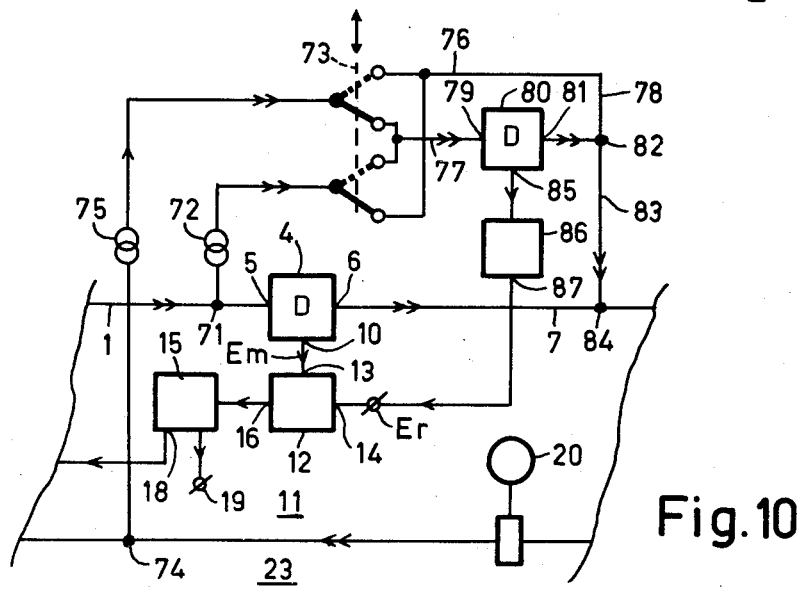
FIG. 10 shows a part of FIG. 2, equipped with a second control loop according to the invention.

FIG. 10 shows an extension of a part of FIG. 2 to illustrate the possibility of continuously measuring the fluid flow and yet introducing a compensation for zero-point drift and sensitivity variation of the detector. A known part of the flow in line 1 is discharged at a branch 71 before inlet 5 of detector 4 by means of a flow controller 72 and is supplied to a first section of a duel switching valve 73. Moreover, a known part of the calibration flow in calibration line 23 is discharged at a branch 74 by a flow controller 75 and is supplied to the second section of switching valve 73. The switching valve has two outlets of which one outlet 76 is connected to a discharge line 78 and the other outlet 77 is connected to the inlet 79 of a second detector 80. The fluid flow outlet 81 of detector 80 is connected to a common point 82, to which line 78 is also connected, so that via a line 83 the common flows of controllers 72 and 75 can be supplied to a branch 84 in line 7. The Figure shows that either the measuring flow from controller 72 is discharged and the calibration flow from controller 75 is supplied to the detector, as shown, or that in the other position of valve 73 the calibration flow is discharged and the measuring flow is supplied to the detector. By means of an associated mechanism the valve 73 changes over from one position to the other position at regular intervals. Thus, either the calibration flow or the measuring flow will produce a measuring signal at the measuring output 85 of the detector 80. An electrical controller 86 which is connected to the measuring output 85 of the detector 80 is adapted so that it can measure whether the measuring voltage at output 85 contains an a.c. component with the frequency of the switching rate of valve 73. In that case the two flows through controllers 72 and 75 will not contain an equal amount of constituents and will consequently produce a different measuring signal. Since a calibration flow is taken as a reference, which in the present example is provided by the flow controller 75, and the measuring flow from controller 72 should be equal thereto, because then a constant amount of constituents is supplied to inlet 5 of the detector 4, the electrical controller 86 will produce an output signal for control purposes which should assume such a value that said alternating component in the measuring signal at output 85 is minimized. For this, output 87 of controller 86 is connected to input 14 of the comparator circuit 12, and said output signal of controller 86 equals the reference voltage $E_r$. It has already been noted that the loop with controller 72, valve 73, detector 80 and controller 86 should have a small bandwith, i.e. should respond slowly, because the normal fluctuations in the amount of constituents which are supplied to the detector 4, must be eliminated by the measuring control loop with control device 11 and not by the described auxiliary control loop. This last-mentioned loop should merely provide a reference for the response of the detector 4 to a constant amount of constituents to be measured, i.e. inclusive of zero-point drift and sensitivity variation. In spite of the additional number of components which are required for the auxiliary control loop, this complete system for measuring constituents in a fluid yields the advantage that continuous measurement is possible without calibration interruptions, so that also detectors which vary more readily may be used.

The auxiliary control system of FIG. 10 may of course be used in the embodiments of the apparatus as described with reference to the preceding Figures. In that case some adaptations in respect of the calibration flow and measuring flow to be supplied will then be necessary. Preferably, the calibration flow is to be derived from the same calibration source 20.

Furthermore, it is to be noted that it is common practice to use the same fluid constituents to be measured as calibration constituents for the calibration source. However, it is also possible to select a detector which supplies a positive measuring voltage for a specific type of constituents and a negative voltage for a different type. By selecting the one type for the measurement and the other type for the calibration, noise problems in the control system, which might give rise to negative control signals for the flow controllers, may also be avoided.

It will be evident that the methods and apparatus according to the invention are highly suited for use in unattended measuring stations for water and air pollutions, for which reliable and low-maintenance measuring systems are required.

What is claimed is:

1. A method of continuously and quantitatively determining at least one constituent of a fluid which is passed through a detector, in which a measuring signal is obtained at output terminals of the detector, which signal is a measure of the amount of constituents supplied to the detector, comprising continuously replenishing the amount of constituents to be measured in the fluid with a known amount of the constituents, supplying at least a part of the constituents of the resulting mixture to the detector, comparing the measuring signal from the detector with a reference signal and adjusting by a control device the amount of constituents supplied to the detector so as to minimize a difference between measuring signal and reference signal, the setting of the control device being a measure of the amount of constituents to be measured.

2. A method as claimed in claim 1, comprising in addition cleaning the fluid of the constituents to be measured by means of a filter and subsequently adding the known amount, and employing the resultant measuring signal from the detector as a reference signal.

3. A method as claimed in claim 1, comprising passing a known portion of the part of the constituents of the resulting mixture which is supplied to the detector to a measuring circuit which includes a second detector, to which alternately said known portion and a known calibration amount of constituents is supplied, the detector producing a measuring signal which contains an a.c. component if the concentrations in the two flows of fluid are not equal, and adjusting said reference signal by means of an electrical controller so that the a.c. component is minimized.

4. A method as claimed in claim 1, wherein the calibration amount is variable and is adjusted by the control device, after which the resulting mixture is passed through the detector.

5. A method as claimed in claim 1, wherein the calibration amount is constant and the control device includes an adjusting element, said adjusting element ensuring that a part of the constituents of the mixture is passed through the detector.

6. A method as claimed in claim 5, wherein said supplying step comprises supplying a part of the mixture directly to the detector, and comprising conducting the other part through a fluid flow controller and an absorption filter, the adjusting element being the fluid flow controller and the absorption filter absorbing the constituents.

7. A method as claimed in claim 6, comprising dividing the mixture into two parts, supplying one part directly to the detector and bypassing the other part around the detector.

8. A method as claimed in claim 7, wherein the division of the mixture into two parts is determined by a fluid flow controller as adjusting element.

9. An apparatus for continuously and quantitatively determining at least one constituent of a fluid, comprising a detector having an inlet connected to a supply line and an outlet connected to a discharge line; a first fluid flow controller means in the discharge line for sustaining a fluid flow through the detector from a supply compartment, the fluid constituents to be measured producing a measuring a signal at output terminals of the detector; and a calibration source for supplying a known amount of constituents, wherein the apparatus also comprises a control device having a reference source for a reference signal, a comparator circuit, an electrical controller and an adjusting device, a first input of the comparator circuit being connected to the output terminals of the detector, a second input being connected to the reference source, the output being connected to the input of the controller and the output of the controller being connected to the adjusting device; the supply line comprising a first branch to which a calibration line is connected which includes the calibration source, the adjusting device comprising a second fluid flow controller, which influences the amount of constituents supplied to the detector, and wherein the first fluid-flow controller means is included in the discharge line.

10. An apparatus as claimed in claim 9, wherein the calibration line comprises an inlet, a first branch and a third fluid flow controller therebetween, a first absorption filter which absorbs the constituents, the calibration source and a first self-diluting system which consists of two parallel branches; a first branch directly transferring the calibration flow of fluid, and the second branch in the direction of flow first including a second fluid flow controller and then a second absorption filter.

11. An apparatus as claimed in claim 10, wherein the inlet of the calibration line is connected to a second branch which is located in the discharge line between the detector and the first fluid-flow controller.

12. An apparatus as claimed in claim 10, wherein the inlet of the calibration line is connected to a third branch which is located in the supply line between the inlet of said line and the first branch.

13. An apparatus as claimed in claim 9, wherein the calibration source is directly connected to the first branch through the calibration line, between this branch and the detector a self-diluting system is included in the supply line, which system consists of two parallel branches, a first branch directly transferring the flow of fluid and the second branch in the direction of flow first including the second fluid flow controller and subsequently a third absorption filter.

14. An apparatus as claimed in claim 9, wherein the calibration source is directly connected to the first branch through the calibration line, and between this branch and the detector a fourth branch is included in the supply line, which is connected by a line to a fifth branch which is located in the discharge line between the detector and the first fluid flow controller.

15. An apparatus as claimed in claim 14, wherein the second fluid flow controller is located in the discharge line between the detector and the fifth branch.

16. An apparatus as claimed in claim 14, wherein the second fluid flow controller is located in said line connected to the fifth branch.

* * * * *